United States Patent
Bolash et al.

(10) Patent No.: US 6,914,684 B1
(45) Date of Patent: Jul. 5, 2005

(54) METHOD AND APPARATUS FOR DETECTING MEDIA TYPE

(75) Inventors: John Philip Bolash, Lexington, KY (US); Mahesan Chelvayohan, Lexington, KY (US)

(73) Assignee: Lexmark International, Inc., Lexington, KY (US)

( * ) Notice: Subject to any disclaimer, the term of this patent is extended or adjusted under 35 U.S.C. 154(b) by 365 days.

(21) Appl. No.: 09/899,632

(22) Filed: Jul. 5, 2001

(51) Int. Cl.[7] .......... G01B 11/30; G01N 21/00; G01N 21/47; G01N 21/86; B41J 2/01
(52) U.S. Cl. .......... 356/600; 356/73; 356/446; 250/559.4; 347/105
(58) Field of Search .......... 356/237.2, 445, 356/446, 73, 600; 347/16, 101, 105; 358/434; 399/16, 389; 271/258.01; 250/559.4, 559.44, 559.46, 559.16, 559.17, 559.18; 355/407, 408

(56) References Cited

U.S. PATENT DOCUMENTS

| | | | |
|---|---|---|---|
| 3,827,808 A | 8/1974 | Cho | |
| 4,159,874 A | 7/1979 | Dearth et al. | |
| 4,319,847 A * | 3/1982 | Howarth | 356/431 |
| 4,540,887 A | 9/1985 | Minerd et al. | |
| 4,577,096 A | 3/1986 | Beery et al. | |
| 4,685,982 A | 8/1987 | Kucheck | |
| 4,690,577 A | 9/1987 | Kikuchi et al. | |
| 4,750,140 A * | 6/1988 | Asano et al. | 382/108 |
| 4,815,858 A * | 3/1989 | Snail | 356/446 |
| 4,945,253 A | 7/1990 | Frohardt | |
| 4,952,061 A | 8/1990 | Edgar | |
| 5,005,049 A | 4/1991 | Matsushita | |
| 5,084,627 A | 1/1992 | Ueki et al. | |
| 5,139,339 A * | 8/1992 | Courtney et al. | 356/446 |
| 5,260,584 A | 11/1993 | Popson et al. | |
| 5,283,424 A | 2/1994 | Acquaviva et al. | |
| 5,329,338 A | 7/1994 | Merz et al. | |
| 5,401,977 A | 3/1995 | Schwarz | |
| 5,455,659 A | 10/1995 | Ishizu et al. | |
| 5,751,443 A | 5/1998 | Borton et al. | |
| 5,754,213 A * | 5/1998 | Whritenor | 347/218 |
| 5,764,251 A * | 6/1998 | Hashimoto | 347/16 |
| 5,844,682 A | 12/1998 | Kiyomoto et al. | |
| 5,859,440 A | 1/1999 | Acquaviva | |
| 5,925,889 A | 7/1999 | Guillory et al. | |
| 5,934,140 A | 8/1999 | Jackson et al. | |
| 6,006,668 A | 12/1999 | Rehmann | |
| 6,018,164 A | 1/2000 | Mullens | |
| 6,079,807 A | 6/2000 | Lindstrom et al. | |
| 6,561,643 B1 * | 5/2003 | Walker et al. | 347/105 |
| 6,590,223 B1 * | 7/2003 | Chelvayohan | 250/559.4 |
| 6,600,167 B2 * | 7/2003 | Sano | 250/559.11 |
| 6,677,603 B2 * | 1/2004 | Yanagiuchi | 250/559.4 |
| 6,725,207 B2 * | 4/2004 | Swimm | 706/20 |

* cited by examiner

Primary Examiner—Zandra V. Smith
Assistant Examiner—Gordon J. Stock, Jr.
(74) Attorney, Agent, or Firm—Stass & Halsey LLP

(57) ABSTRACT

Media manipulation and sensing apparatuses having a media type detector and method for media type detection, wherein non-linear characteristics of light sensors used for measuring a media type are compensated for by adjusting for the light flux capability of one of the sensors to be greater than the light flux capability of another sensor, such that the ratio between the two sensors accurately represents the glossiness of an illuminated media. An algorithm technique is applied such that a value for a detected sensor signal, which falls in a non-linear range of a sensor characteristic curve, is extrapolated to a value that corresponds to a position on a projection of a linear portion of the sensor characteristic curve, and thereby measuring the glossiness based on the extrapolated sensor signal.

25 Claims, 6 Drawing Sheets

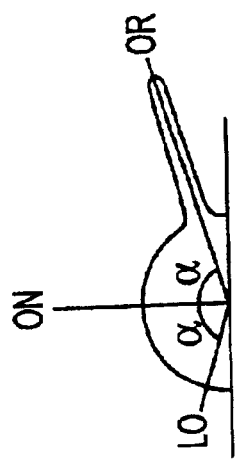
FIG. 3A (PRIOR ART)
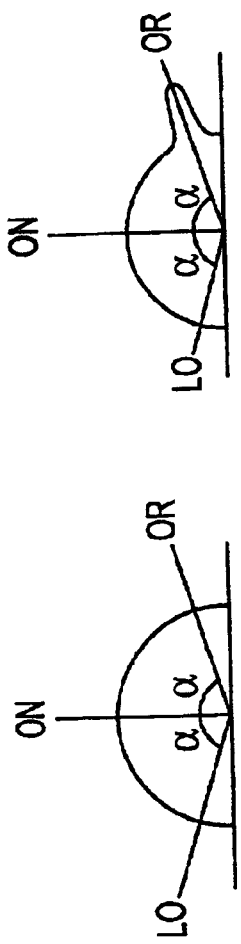
FIG. 3B (PRIOR ART)
FIG. 3C (PRIOR ART)
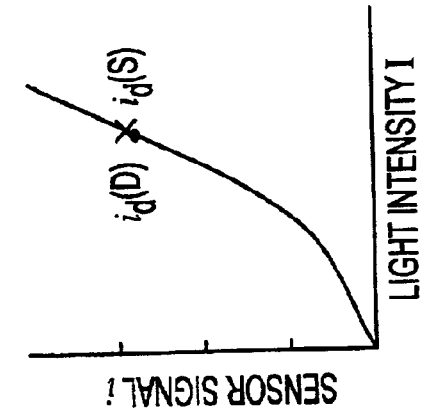
FIG. 4A (PRIOR ART)
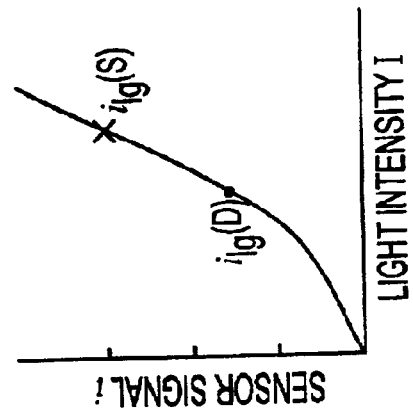
FIG. 4B (PRIOR ART)
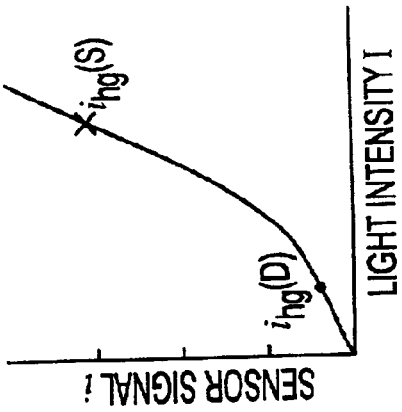
FIG. 4C (PRIOR ART)

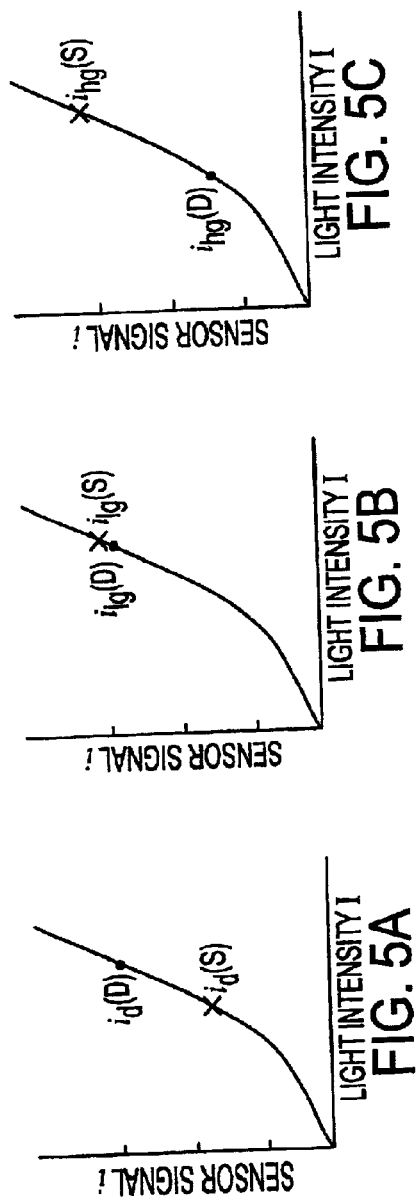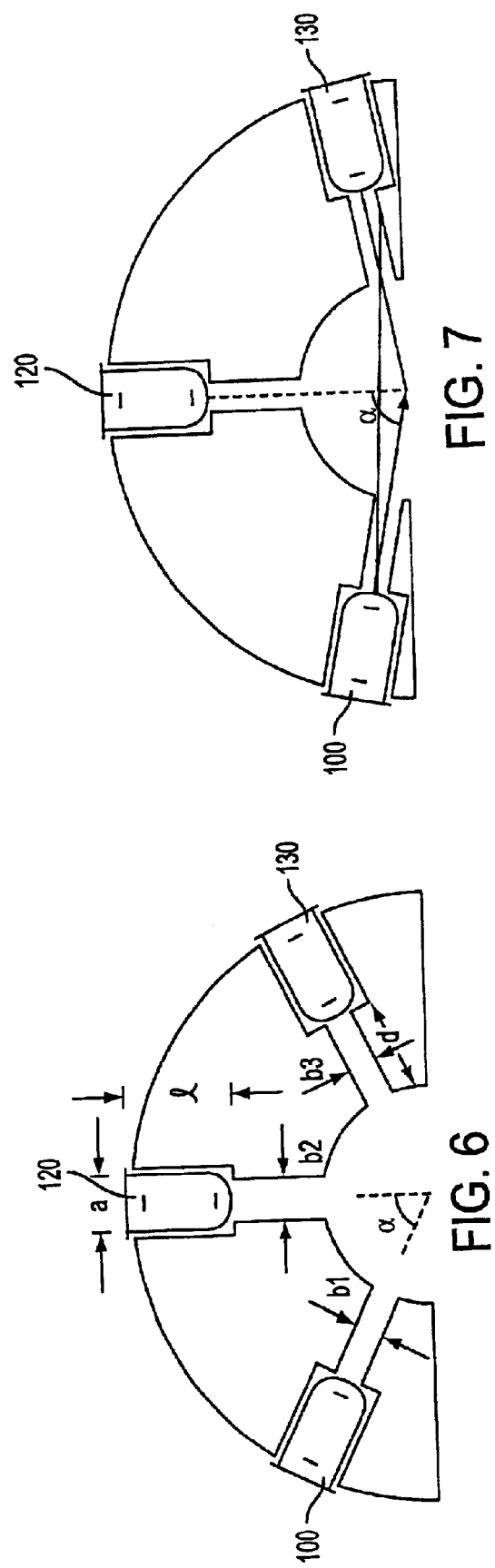

METHOD AND APPARATUS FOR DETECTING MEDIA TYPE

BACKGROUND OF THE INVENTION

1. Field of the Invention

The present invention relates to a method and apparatus for detecting the media type of a media. More particularly, the present invention relates to a method and apparatus for detecting a type of media based on a glossiness of the media while adjusting for the nonlinear characteristics of sensors used for measuring the glossiness.

2. Description of the Related Art

Typically, media manipulation or sensing apparatuses operate in different modes based on the presence of different types of media. A media manipulation or sensing apparatus may operate in a different mode if the media type is of a high glossy type, like a transparency media type, compared to when the media type is of a low glossy type, like plain paper. For example, in a printing environment, certain parameters of printing onto a media are adjusted based upon the media type determination. Typically, in the printing environment, a user must manually indicate to a printing apparatus what type of media is present. Alternatively, some printing systems "pick," or grab, the media and advance it through the printing system, and then determine the type of media, format the parameters for printing thereon, and proceed with printing onto the media. However, these systems are not usually desirable as the printing system cannot know what type of media is being picked until after advancing the media, which reduces the throughput of media in the printing system.

Optical methods and apparatuses previously implemented for such media type detection have included media type detectors having multiple sensors detecting an amount of light reflected off a media. For example, Minerd et al., U.S. Pat. No. 4,540,887, illustrates a media presence detector and Courtney et al., U.S. Pat. No. 5,139,339, utilizes diffusely and specularly arranged sensors in a media type detector. Courtney et al. specifically sets forth discriminating a media type, though the media type discrimination is not based on a ratio of the specular and diffuse light intensities, as done in the present invention. In addition, the following references briefly discuss the non-linearities of sensors used in such media detection applications: Borton et al., U.S. Pat. No. 5,751,443, Whitehouse et al., U.S. Pat. No. 4,218,144, and Watanabe et al., U.S. Pat. No. 5,109,236.

In one media type detector, as illustrated in FIG. 1, when light source 10 irradiates media 5, light reflecting off media 5 is detected by diffuse sensor 20 and specular sensor 30.

The glossiness of media 5 may be determined by measuring the ratio of the detected diffuse I(D) and specular I(S) light intensities via typical transducers, such as photo transistors. These transducers or sensors convert the light intensities I(D) and I(S) to output signals i(D) and i(S), respectively, with i(D) and i(S) typically being current signals, which vary proportionally to the input light intensities input to them (I(D) and I(S) respectively). Glossier papers tend to reflect specularly more than diffusely, thus a media detecting ratio i(S)/i(D) can be used to determine the glossiness of media 5, from which the type of media can be determined. Typically, before measuring the media detecting ratio i(S)/i(D), a ratio table is developed, wherein media detecting i(S)/i(D) ratios are stored for a corresponding multitude of different types of media By referencing back to this ratio table after measuring media detecting ratio i(S)/i(D), corresponding types of media can be differentiated. Typically the determination of a media type according to the media detecting ratio i(S)/i(D) can be accomplished in a determining portion of an overall system by hard wiring or software in a processing unit.

As illustrated in FIG. 1, diffuse sensor 20 is typically, but is not required to be, arranged at a position normal from media 5 and specular sensor 30 should be arranged at a position along a positive incidence angle $\alpha$ from normal, with light source 10 being arranged at a position along a negative incidence angle $\alpha$ from normal. FIG. 2 illustrates the variation of the ratio i(S)/i(D) and glossiness for a large incidence angle $\alpha'$ and a small incidence angle $\alpha''$. Typically, a media type detector with a large incidence angle $\alpha'$ has better gloss resolution and is usually preferred in media type detection. However, such systems will have very small diffuse sensor signal i(D) in the presence of highly glossy media Even with low gloss media, diffuse sensor signal i(D) will be lower than specular sensor signal i(S).

FIGS. 3A–3C illustrate angular distributions of reflected light intensities for different types of media, where the illustration of LO represents the incident light, OR represents specularly reflected light, and ON represents the normal to the reflecting surface. With a perfectly diffuse media type in FIG. 3A, the intensity distribution is substantially equal in all reflected directions. Whereas, with low glossy and high glossy media types shown in FIGS. 3B and 3C, respectively, the intensity in the specular direction is larger than the reflected intensity in non-specular directions.

Corresponding to the different media types in FIGS. 3A–3C, FIGS. 4A–4C respectively illustrate operating points for both diffuse sensor signal i(D) and specular sensor signal i(S) on sensor output signal i vs. sensor input light intensity I characteristic curves. In these illustrations, the aperture of both the diffuse and specular sensors are of equal dimensions and the sensors have equal sensitivity. FIG. 4A shows the operating points of both sensors' signals $i_d(S)$ and $i_d(D)$ as being equal and in a linear region of the sensor characteristic curve for a perfectly diffuse media. FIG. 4B shows the operating point of the specular sensor signal $i_{lg}(S)$ as being in a linear region and the operating point of the diffuse sensor signal $i_{lg}(D)$ as moving down the sensor characteristic curve close to a non-linear region for a low gloss media Lastly, FIG. 4C shows that in a high glossy media type the operating point of the diffuse sensor signal $i_{hg}(D)$ has moved entirely to the non-linear region of the sensor characteristic curve, while the specular sensor signal $i_{hg}(S)$ operating point is in a linear region of the sensor characteristic curve. When either diffuse or specular sensor signal operating points move into a non-linear region of the sensor characteristic curve, the resulting ratio measurements are not accurate for media type detection.

In the illustrations of FIGS. 4A–4C, it is noted that specular sensor signal i(S) has been shown as always being in a stationary operating position, whereas FIGS. 3A–3C indicate that the specular intensity I(S) is actually increasing. To prevent specular intensity I(S) from saturating detector circuitry, specular intensity I(S) is maintained at a certain level by varying the light source intensity. The light source is typically, but not limited to, an infrared LED, and is pulsed during measurements using a Pulse Width Modulation (PWM) signal. The diffuse and specular sensors are usually phototransistors and the media type detector typically amplifies and filters their outputs to get DC outputs when the PWM is being performed. By changing the duty cycle of the PWM for the light source, the light intensity can be varied, and thus prevent the specular sensor signal i(S) from saturating the media type detector circuitry. Thus, the diffuse sensor signal, i(D), actually moves down the sensor characteristic curves in FIGS. 4A–4C because the intensity of the light source has been decreased, which undesirably forces the diffuse sensor signal, i(D), into the non-linear region of the sensor characteristic curve. Additional methods for adjusting the strength of the light source are also available without using a PWM method.

Therefore, to overcome these non-linear operating point problems, the present invention sets forth an operating point adjusting method and apparatus to keep the operating points of diffuse sensor signal i(D) and specular sensor signal i(S) in the linear region, and thus produce accurate media detecting ratios of i(S)/i(D). In addition, in solving these aforementioned problems, the present invention allows for the use of a wider variety of sensors and thus achieve lower sensor cost due either to higher yields of a particular sensor part from a single supplier or the ability to use different sensor parts from different suppliers.

SUMMARY OF THE INVENTION

An object of the present invention is to provide a media type detector which adjusts for the non-linear characteristics of sensors used for measuring a glossiness of the media.

Another object of the present invention is to provide a media manipulation apparatus, having a media type detector including, a light source to illuminate a media, a specular light sensor, and a first light sensor, wherein the first light sensor has a higher light flux capability compared to the specular light sensor. The media manipulation apparatus further includes a determination unit to determine a media type of the media based on a signal ratio of a detected specular light sensor intensity and a detected first light sensor intensity.

A further object of the present invention is to provide a media sensing apparatus, having a media type detector including, a light source to illuminate a media, a specular light sensor, and a first light sensor, wherein the first light sensor has a higher light flux capability compared to the specular light sensor. The media sensing apparatus further includes a determination unit to determine a media type of the media based on a signal ratio of a detected specular light sensor intensity and a detected first light sensor intensity.

Another object of the present invention is to provide a media type detector, including a specular light sensor, and a first light sensor, wherein the first light sensor has a higher light flux capability compared to the specular light sensor, such that, upon an illumination of a media, a signal ratio of a detected specular light sensor intensity and a detected first light sensor intensity is determinative of a media type of the media Another object of the present invention is to provide a media type detector, including a specular light sensor, and a first light sensor, wherein the first light sensor has a higher light flux capability compared to the specular light sensor, such that, upon an illumination of a media, when a signal of a detected first light sensor intensity falls within a linear characteristic range of the first light sensor, a signal ratio of a detected specular light sensor intensity and the detected first light sensor signal is determinative of a media type of the media.

Another object of the present invention is to provide a media type detection method, including measuring a plurality of light intensities radiating off of a media, including a specular light sensor intensity by a specular light sensor, where the specular light sensor has a smaller light flux capability than a first light sensor measuring one of the plurality of light intensities other than the specular light sensor intensity, and determining a media type of the media based on a signal ratio of the specular light sensor intensity and at least the first light sensor intensity.

A further object of the present invention is to provide a media type detection method, including measuring at least first and second light intensities radiating off of a media, determining if one of the first and second light intensities does not fall within a linear region of a characteristic curve of a light sensor, and determining a media type of the media based on a signal ratio of at least the first and second light intensities if it is determined that at least both of the first and second light intensities falls within the linear region of the characteristic curve of a light sensor. Otherwise, the media type detection method includes determining a media type of the media by extrapolating one of the first or second light intensities, which does not fall within the linear region of the characteristic curve of a light sensor, by projecting the one of the first or second light intensities onto a linear curve and then determining the media type based on a signal ratio of the one of the first or second light intensities that was not projected and the projected one of the first or second light intensities.

BRIEF DESCRIPTION OF THE DRAWINGS

Advantages of the invention will become apparent and more readily appreciated for the following description of the preferred embodiments, taken in conjunction with the accompanying drawings of which:

FIGS. 3A–3C are illustrations of angular distributions of reflected light intensities for, respectively, perfectly diffuse media, low glossy media, and high glossy media;

FIGS. 4A–4C are graphs illustrating conventional operating points for diffuse and specular sensor signals for, respectively, perfectly diffuse media, low glossy media, and high glossy media, on a sensor characteristic curve;

FIGS. 5A–5C are graphs illustrating operating points for diffuse and specular sensor signals for, respectively, perfectly diffuse media, low glossy media, and high glossy media, on a sensor characteristic curve, with an increased diffuse light flux;

FIG. 6 is an illustration of an embodiment of the present invention for a media manipulation apparatus showing the diameter of the aperture of the diffuse sensor being larger than that of the specular sensor, FIG. 7 is an illustration showing the results of a configuration when the incidence angle is too large;

DETAILED DESCRIPTION OF THE PREFERRED EMBODIMENTS

Figure 1:
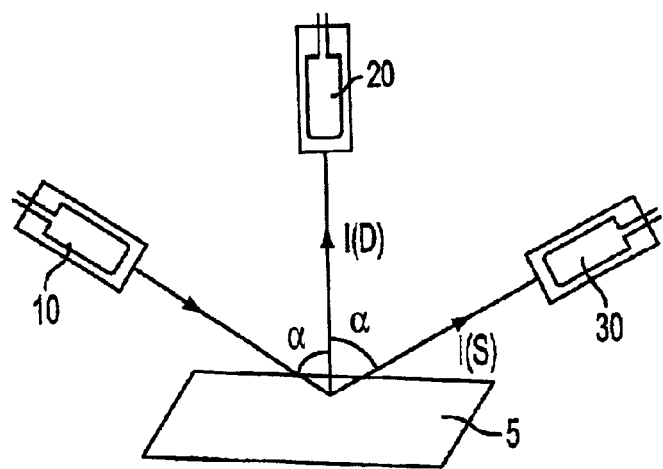
FIG. 1 is an illustration of a media type detector having a light source, a diffuse sensor, and a specular sensor.
Figure 2:
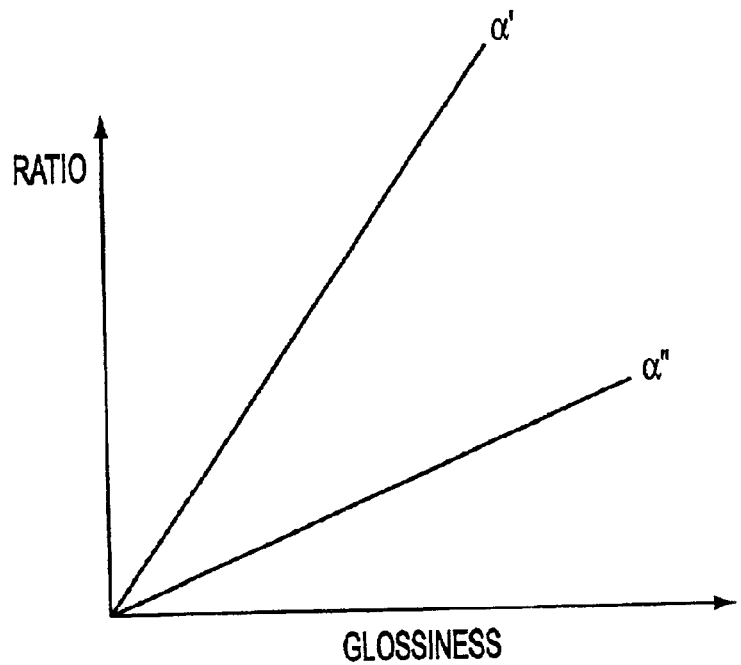
FIG. 2 is a graph showing variation of the intensity ratio and glossiness for a large incidence angle and a small incidence angle.

Reference will now be made in detail to the preferred embodiments, examples of which are illustrated in the accompanying drawings. In accordance with the preferred embodiments, there is provided a method and apparatus for providing accurate media type detection.

As noted above, in the traditional sensor configuration for a media type detector, the values of diffuse sensor signal i(D) and/or specular sensor signal i(S) may fall along non-linear operating points of a corresponding sensor curve, thereby preventing accurate media detecting ratio measurements and accurate media type determinations.

Through research and experimentation, it has been determined that the above non-linear operating point problem may be overcome by moving the diffuse sensor signal i(D) operational point, shown in FIG. 4C, further up the sensor characteristic curve and out of the non-linear region. The operational point for the diffuse sensor signal i(D) can be moved up the curve by relatively increasing the diffused light flux entering into the diffuse sensor. A relatively larger diffused channel aperture, while not changing the size of the specular channel aperture, could be used to increase the diffuse sensor signal i(D) value and allow for both diffuse sensor signal i(D) and specular sensor signal i(S) operational points to fall in a linear region of the sensor characteristic curves of each sensor. With the diffuse sensor having a larger aperture than the specular sensor, the diffuse sensor could be considered as having a larger light flux capability than that of the specular sensor.

FIGS. 5A–5C illustrate results of the above mentioned movement of the diffuse sensor signal i(D) operational point up the sensor characteristic curve when the diffuse sensor aperture is wider than the specular sensor aperture. Similar to FIGS. 4A–4C, FIGS. 5A–5C show the operational points of the specular and diffuse sensor signals on sensor characteristic curves for different types of media, with FIG. 5A being a perfectly diffuse media, FIG. 5B being a low glossy media, and FIG. 5C being a high glossy media.

FIG. 6 illustrates an embodiment of the present invention for a media manipulation apparatus where the size of the diffused channel aperture is greater than the size of the specular channel aperture. In this embodiment, the media type detector has been designed to be embodied in a small package, using commercially available low cost optical components in a new and novel manner. Specifically, FIG. 6 illustrates an optimized media detector design using T-1 size optical components. Each sensor is placed in an approximately 3 mm diameter (a)×5 mm long (1) cylindrical cavity. The diameter of each individual light channel (b1, b2, and b3) is optimized by limiting the acceptance angle of the sensors, and thereby improve the resolution of the media sensor. As illustrated in FIG. 6, the diameter of a light channel for light source 100 and specular sensor 130 are about 1.3–1.7 mm (b1 and b3), and 2.2–2.6 mm (b2) for diffuse sensor 120, with the length of the channel (d) being approximately 5 mm. FIG. 6 also illustrates a configuration of light source 100, diffuse sensor 120, and specular sensor 130, where each component is arranged at equal radii from the light incidence point on the media surface. Therefore, the present embodiment illustrated in FIG. 6 includes a "rainbow" shaped interior surface. This rainbow surface allows for a sufficient amount of light to reflect off the surface of the media to be adequately detected by the diffuse and specular sensors.

In this embodiment, the incidence angle a has been chosen to be 65°. The incidence angle has been chosen so that it is large enough to increase the glossiness resolution and small enough to keep specular sensor 130 from the direct view of light source 100. FIG. 7 illustrates that if specular sensor 130 were in the direct view of light source 100, i.e., if incidence angle α is too large, then specular sensor 130 may inappropriately receive specular reflected light as well as light radiating directly from light source 100. Preferably, the incidence angle α may be 65°±3°.

Figure 8A:
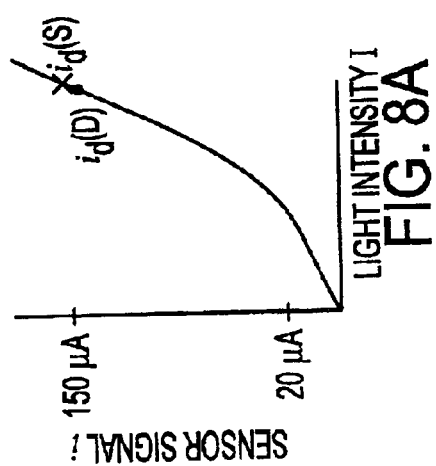
FIGS. 8A–8C are graphs illustrating experimental operating points for diffuse and specular sensor signals for, respectively, perfectly diffuse media, low glossy media, and high glossy media, on a sensor characteristic curve, with the diffuse and specular sensors having the same aperture diameter.
Figure 8B:
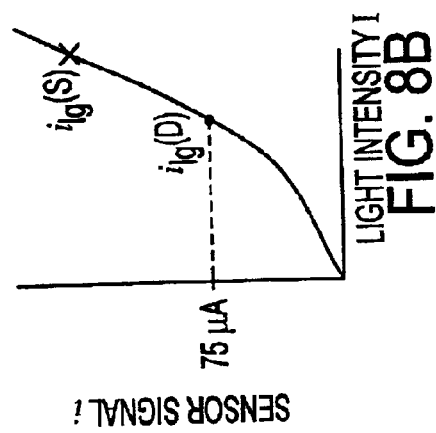
Figure 8C:
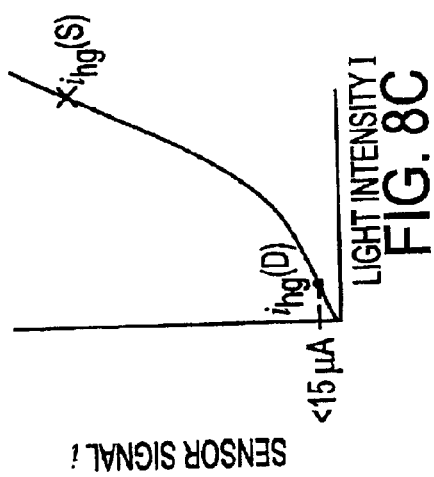

As noted above, when the diameter of the aperture of diffuse sensor 120 is the same as the aperture of specular sensor 130, the diffuse sensor signal i(D) operational point may lie in a non-linear region of the sensor characteristic curve. FIGS. 8A–8C illustrate the experimental operational point results for different media when the above sensor configuration is used and when both the diffuse and specular apertures have a 1.5 mm diameter, for perfectly diffuse, low glossy, and high glossy media types, respectively. As shown in FIGS. 8A–8C, the phototransistors are non-linear below 20 $\mu$A. As shown in FIGS. 8A–8C, specular sensor signal i(S) operational point is maintained near 150 $\mu$A to keep specular sensor signal i(S) in the measurable range of the detector circuitry. In addition, FIG. 8B shows the diffuse sensor signal $i_{lg}$(D) operational point being near 75 $\mu$A, and FIG. 8C shows the diffuse sensor signal $i_{hg}$(D) operational point being less than 15 $\mu$A, and thus within the non-linear region of the sensor characteristic curve.

Figure 9A:
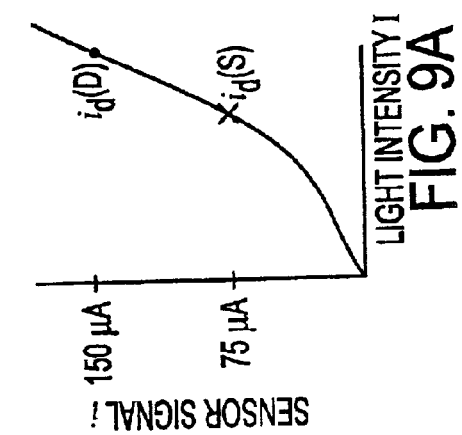
FIGS. 9A–9C are graphs illustrating experimental operating points for diffuse and specular sensor signals for, respectively, perfectly diffuse media, low glossy media, and high glossy media, on a sensor characteristic curve, with an increased diffuse light flux capability.
Figure 9B:
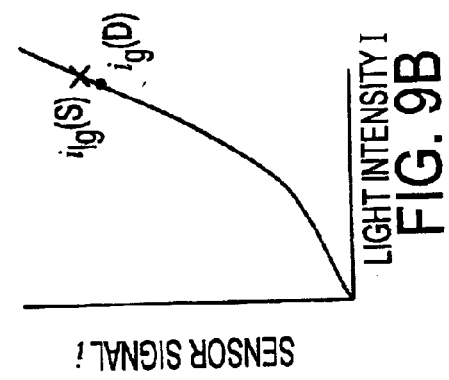
Figure 9C:
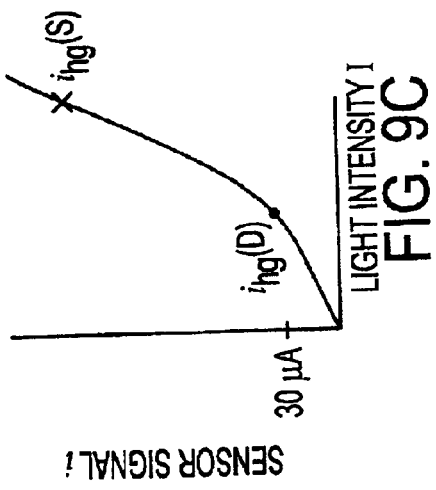

Similar to FIGS. 8A–8C, FIGS. 9A–9C illustrate sensor characteristic cure results using the present embodiment configuration, with the aperture diameter of diffuse sensor 120 being 2.4 mm and the aperture diameter of specular sensor 130 being 1.5 mm. As shown in FIGS. 9A–9C, the maximum sensor signal operational point is 150 $\mu$A, with the diffuse sensor signal i(D) operational point being kept within the linear region of the sensor curve, e.g., $i_{hg}$(D) being near 30 $\mu$A when the media is of a high glossy type, instead of less than 15 $\mu$A where it was when the apertures were equal.

In the above embodiment, although specific incidence angles and aperture dimensions have been discussed, the present invention is not limited thereto. Based on the application and the desired amount of resolution, the incidence angle and aperture dimensions could be adjusted further as long as sufficient amounts of light can be detected by diffuse sensor 120 and specular sensor 130 and the sensors do not see direct light from the light source.

Although the above embodiments have set forth a solution of previous non-linear problems by increasing the diffuse flux amount, when very reflective media are present in the media type detector path the amount of specular light detected may be so substantial that the diffuse sensor signal i(D) may still be in a non-linear region of the sensor characteristic curve. Typically, as noted above, when the sensors and corresponding components are limited in their maximum detected value amount, the strength of the light source is adjusted to keep the sensor signals, usually the specular sensor signal i(S), below the maximum value allowed by the detection circuitry. However, when the media is very reflective, e.g., when several transparencies are stacked back to back, the light source may be adjusted to such a low strength that the operational point of diffuse sensor signal i(D) is moved sufficiently into the non-linear value region of the sensor characteristic curve that even the aforementioned increase in diffuse flux capability of the diffuse sensor cannot fully move the operational point back into a linear region of the sensor characteristic curve.

In this situation, it may be necessary to also implement an algorithm technique to calculate the appropriate media defining ratio. By using a relationship between the duty cycle of the PWM, controlling the light source, when only one sensor signal operational point is in a linear region of the sensor characteristic curve and the duty cycle necessary to move the other non-linear region operational point into a linear region, an appropriate media defining ratio can be calculated. For example, if the operational point for the diffuse sensor signal i(D) were in the non-linear region for a light source duty cycle DO, the duty cycle for the light source could be changed from DO to D1, for example, to move the corresponding operational point of the diffuse sensor signal i(D) into a linear region. The new operational point of the diffuse sensor signal i(D)* is detected and multiplied by the ratio of DO to D1 to derive an extrapolated diffuse sensor signal i(D) for use in the media detecting ratio i(S)/i(D). By multiplying the diffuse sensor signal i(D)* by the ratio of the PWM duty cycles, DO/D1, an operational point for diffuse sensor signal i(D) can be extrapolated to a position on the sensor characteristic curve by projecting where the operational point would be if the sensor did not have such a non-linear region, thereby ignoring the non-linear region of the sensor characteristic. The change in the duty cycle may also be increased to a maximum amount and the algorithm initiated even if the diffuse sensor signal i(D) is not in a linear region. As recited herein, the use of DO and D1 to represent duty cycles is not limited thereto, as DO and D1 may be merely indicative of any two differing levels of light source intensity. The above algorithm is not limited to utilizing the ratio of duty cycle, but rather is descriptive of extrapolating the non-linear operational point to a projected operational point and utilizing that projected operational point in the media detecting ratio. Of course, in the above algorithm technique, measurement of the sensor corresponding to the higher of the two sensor values will be ceased while the smaller value is increased into the linear region of the curve. Otherwise, the components of the media type detector circuitry may be pushed into a saturation level or overload overall system components.

Although the above algorithm technique has been set forth by extrapolating the non-linear operational point for i(D) to a projected operational point, and utilizing that projected operational point in the media detecting ratio, alternatively, the non-linear operational point for i(D) can be moved into a linear region of the characteristic curve to operating point i(D)*, using the same change of DO to D1, but now i(S), after such a change from DO to D1, can be also be projected onto a continuing linear curve of the characteristic curve at the upper range of the characteristic curve by multiplying i(S) by D1/DO.

Thus, the media detecting ratio can be defined as R=[i (S)]/[i*(D)×DO/D1] or R=[i(S)×D1/DO]/[i*(D)], or to encompass both aforementioned alternative methods R=[i (S)i*(D)]×[D1/DO].

Figure 10:
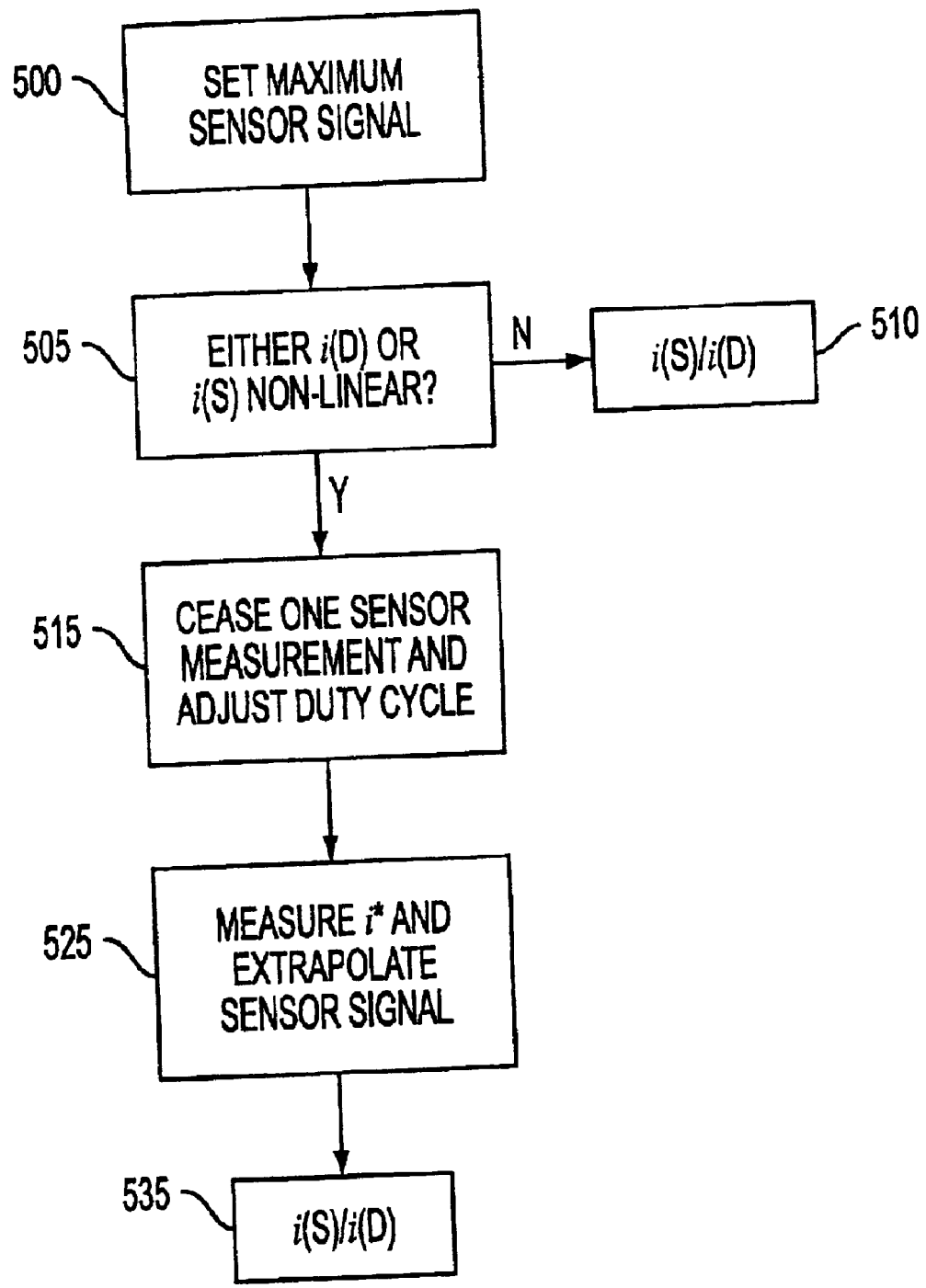
FIG 10 is a flow chart showing the operations for implementing a linear extrapolation algorithm in accordance with embodiments of the present invention.

This algorithm method may be used independently of the aforementioned increase in diffuse flux capability, or alternately the algorithm may be implemented in conjunction therewith. FIG. 10 is a flow chart illustrating operations for implementing an embodiment of the present media detecting ratio measurement. Operation 500 sets forth the aforementioned manipulating the duty cycle of the light source such that the larger of the two sensor signal values, i(D) or i(S), is equal to a set value, preferably the maximum signal value the detector circuitry can handle. Thereafter, in operation 505, the values of both i(D) and i(S) are measured and it is determined whether the smaller of the two sensor values would fall in a non-linear region of the sensor characteristic curve. If not, then in operation 510 the media detecting ratio is measured by calculating the ratio of i(S)/i(D). If the smaller of the two sensor values is in a nonlinear region then in operation 515 the measuring of the larger of the sensor signals is ceased and the duty cycle is adjusted from DO to D1, i.e., until the smaller sensor signal value is in the linear region or the duty cycle reaches its maximum amount. Thereafter in operation 525, the extrapolated smaller sensor signal value is calculated based on the ratio of duty cycles and the value of the smaller sensor signal after being increased by the increased duty cycle. From the extrapolated smaller sensor signal the media detection ratio can be determined in operation 535 by using the extrapolated smaller sensor signal in the i(S)/i(D) equation.

The above disclosed media type detector has been described as being able to detect a type of media, even when a sensor's signal value falls into a non-linear region of a corresponding sensor curve. This media type detector has a multitude of different applications and may be bodily incorporated into a number of different media manipulating or sensing apparatuses.

Figure 11A:
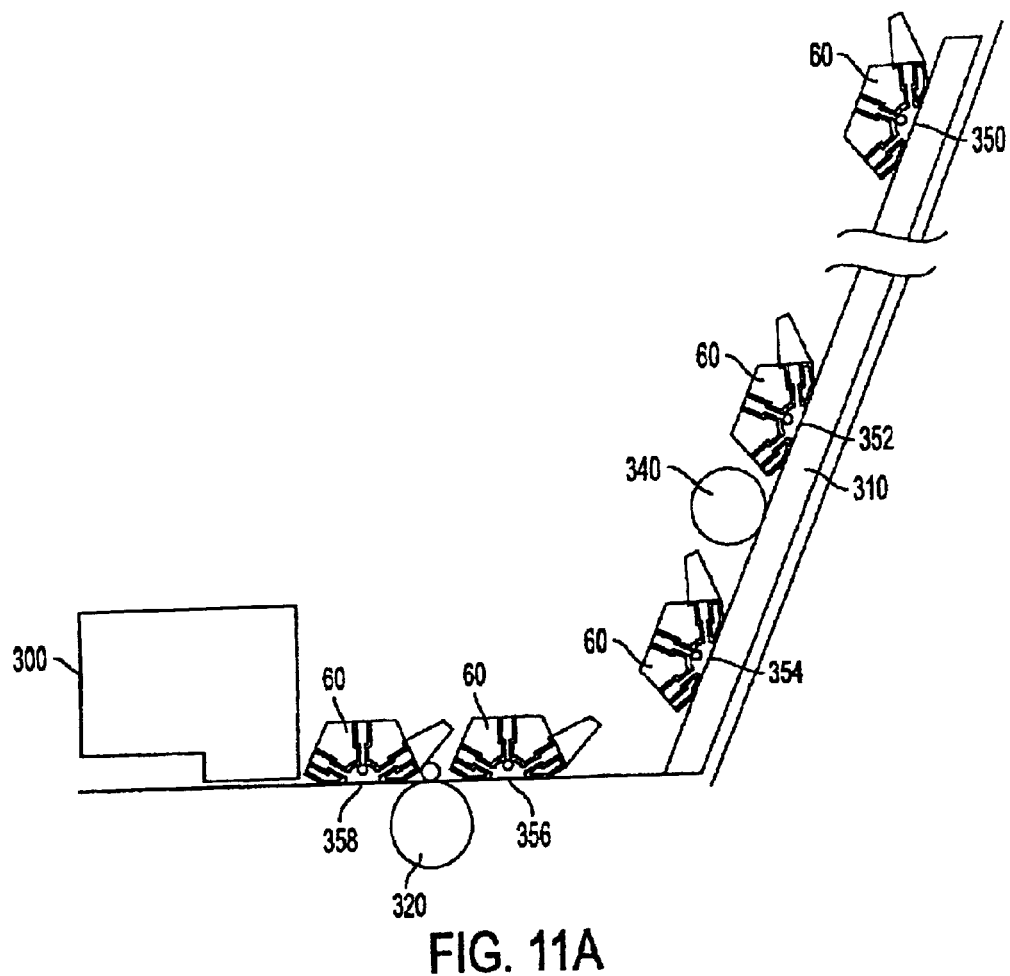
FIGS. 11A and 11B are illustrations showing examples of arrangements of a media type detector in a printing environment.
Figure 11B:
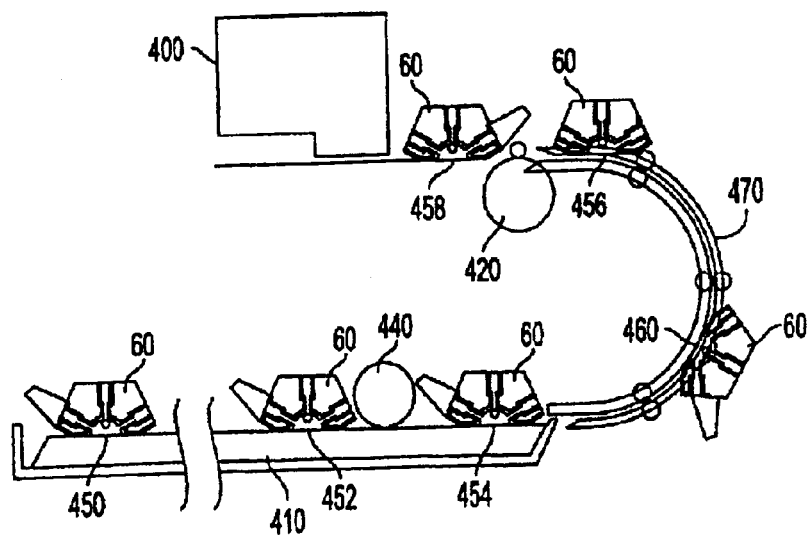

For example, FIGS. 11A and 11B illustrate embodiments where the present invention may be arranged in a printer, for example, in vertical (FIG. 11A) or horizontal sheet (FIG. 11B) feeders. As illustrated in FIGS. 11A and 11B, an embodiment of the present invention has been mounted in a housing sled 60.

FIG. 11A illustrates multiple arrangements within a printer for housing sled 60 in a vertical sheet feeder. As illustrated in FIG. 11A, housing sled 60 can be positioned at the trailing edge 350 of paper stack 310, before picking mechanism 340 on paper stack 310 at position 352, after picking mechanism 340 on paper stack 310 at position 354, before feeding nip 320 at position 356, after feeding nip 320 and before printhead 300 at position 358.

FIG. 11B illustrates multiple arrangements within a printer for housing sled 60 in a horizontal sheet feeder. As illustrated in FIG. 11B, housing sled 60 can be positioned at the trailing edge 450 of paper stack 410, before picking mechanism 440 on paper stack 410 at -position 452, after picking mechanism 440 on paper stack 410 at position 454, in the paper transport path 470 at position 460, before feeding nip 420 at position 456, after feeding nip 420 and before printhead 400 at position 458. Although these arrangements within a printer have been set forth herein, the present invention should not be limited thereto.

Further, FIGS. 11A and 11B have illustrated a printing example of a media manipulation and the present invention should not be limited thereto. For example, additional media manipulation apparatuses could also include photocopiers, inkjet printers, laser printers, paper handlers, as well as additional apparatuses that move or manipulate media, such as a printing thereon, and have a need to determine a media type. Media sensing apparatuses could also include several of the aforementioned apparatuses that manipulate the media as well as perform some type of media sensing, such as photocopiers which scan the media and move the media from place to place, as well as apparatuses that perform sensing without any manipulation, such as flat bed scanners, where the type of media may be of importance, but no manipulation is performed on the media. In the sensing apparatuses, similar to the manipulation apparatuses, it is advantageous to perform the media detecting prior to performing the media manipulation or sensing operations.

Thus, although a few preferred embodiments of the present invention have been shown and described, it would be appreciated by those skilled in the art that changes may be made in these embodiments without departing from the principles and spirit of the invention, the scope of which is defined in the claims and their embodiments.

What is claimed is:

1. A media manipulation apparatus, comprising:
   a media detector including,
   a light source to illuminate a media;
   a specular light sensor, and
   a first light sensor, wherein the first light sensor has a higher light flux capability compared to the specular light sensor; wherein
   the media detector determines a media type of the media based on a signal ratio of a detected specular light sensor intensity and a detected first light sensor intensity.

2. The media manipulation apparatus of claim 1, wherein the signal ratio is a measure of glossiness of the media.

3. The media manipulation apparatus of claim 1,
   wherein a light strength signal provided to the light source, to control a strength of the light source, is increased from D0 to D1 such that a first light sensor signal, detected after said detected first light sensor intensity, falls within a linear region of a sensor characteristic curve of the first light sensor; and
   wherein, if a signal of said detected first light sensor intensity falls within the non-linear region of the sensor characteristic curve of the first light sensor, the media detector bases the media type determination on the detected specular light sensor intensity, the first light sensor signal detected after said detected first light sensor intensity, and a ratio of D0 and D1.

4. The media manipulation apparatus of claim 3, wherein the light strength signal is a PWM signal.

5. The media manipulation apparatus of claim 3, wherein the media type determination based on the detected specular light sensor intensity, the first light sensor signal detected after said detected first light sensor intensity, and the ratio of D0 and D1, is set forth by the equation $R=[i(S)/i^*(D)] \times [D1/D0]$ where R equals a measure of glossiness of the media, $i(S)$ equals a signal representative of the detected specular light sensor intensity, and $i^*(D)$ equals the first light sensor signal detected after said detected first light sensor intensity.

6. A media sensing apparatus, comprising:
   a media detector including,
   a light source to illuminate a media;
   a specular light sensor, and
   a first light sensor, wherein the first light sensor has a higher light flux capability compared to the specular light sensor; wherein
   the media detector determines a media type of the media based on a signal ratio of a detected specular light sensor intensity and a detected first light sensor intensity.

7. The media sensing apparatus of claim 6, wherein the ratio is a glossiness ratio of the media.

8. The media sensing apparatus of claim 6,
   wherein the light strength signal provided to the light source, to control a strength of the light source, is increased from D0 to D1 such that a first light sensor signal, detected after said detected first light sensor intensity, falls within a linear region of a sensor characteristic curve of the first light sensor; and
   wherein, if a signal of said detected first light sensor intensity falls within the non-linear region of the sensor characteristic curve of the first light sensor, the media detector bases the media type determination on the detected specular light sensor intensity, the first light sensor signal detected after said detected first light sensor intensity, and a ratio of D0 and D1.

9. The media sensing apparatus of claim 8, wherein the light strength signal is a PWM signal.

10. The media sensing apparatus of claim 8 wherein the media type determination based on the detected specular light sensor intensity, the first light sensor signal detected after said detected first light sensor intensity, and the ratio of D0 and D1, is set forth by the equation $R=[i(S)/i^*(D)] \times [D1/D0]$ where R equals a measure of glossiness of the media, $i(S)$ equals a signal representative of the detected specular light sensor intensity, and $i^*(D)$ equals the first light sensor signal detected after said detected first light sensor intensity.

11. A media detector, comprising:
    a specular light sensor; and
    a first light sensor, wherein the first light sensor has a higher light flux capability compared to the specular light sensor, such that, upon an illumination of a media, a signal ratio of a detected specular light sensor intensity and a detected first light sensor intensity is determinative of a media type of the media.

12. The media detector of claim 11, wherein the higher light flux capability of the first light sensor is accomplished by an aperture of the first light sensor being larger than an aperture of the specular light sensor.

13. The media detector of claim 11, wherein the specular light sensor, the first light sensor, and a light source are arranged in the media type detector at equal radii from an illumination point of the media.

14. The media detector of claim 13, further comprising a semi-circle shaped interior cavity between the media illumination point and the specular light sensor, the first light sensor, and the light source.

15. A media detector, comprising:
    a specular light sensor; and
    a first light sensor, wherein the first light sensor has a higher light flux capability compared to the specular light sensor, such that, upon an illumination of a media, when a signal of a detected first light sensor intensity falls within a linear characteristic range of the first light sensor, a signal ratio of a detected specular light sensor intensity and the detected first light sensor signal is determinative of a media type of the media.

16. The media detector of claim 15, wherein, if the detected first light sensor signal does not fall within the linear characteristic range of the first light sensor, strength of a light source performing the illumination of the media is increased until a signal of the first light sensor detected, after said detection of the first light sensor intensity, either falls within the linear characteristic range of the first light sensor or the strength of the light source reaches a maximum.

17. The media detector of claim 15, wherein the higher light flux capability of the first light sensor is accomplished by an aperture of the first light sensor being larger than an aperture of the specular light sensor.

18. A media detection method, comprising:
    measuring a plurality of light intensities radiating off of a media, including a specular light sensor intensity by a specular light sensor, where the specular light sensor has a smaller light flux capability than a first light sensor measuring one of the plurality of light intensities other than the specular light sensor intensity; and determining a media type of the media based on a signal ratio of the specular light sensor intensity and at least the first light sensor intensity.

19. The media detection method of claim 18, wherein the smaller light flux capability of the specular light sensor compared to the first light sensor is accomplished by the specular light sensor having a smaller diameter aperture than an aperture of the first light sensor.

20. The media detection method of claim 18, wherein the measuring of the plurality of light intensities radiating off of the media is performed prior to a picking of the media by a media manipulation device.

21. The media detection method of claim 18, wherein the determining of the media type further comprises basing the determination of the media type on an extrapolation of the first light sensor intensity by projecting a signal representative of the first light sensor intensity onto a linear region of a characteristic curve of the first light sensor and by determining a signal ratio of the specular light sensor intensity and the projected first light sensor signal, if it is determined that the first light sensor signal falls within a non-linear region of the first light sensor characteristic curve.

22. A media detection method, comprising:

measuring at least a first and second light intensities radiating off of a media;

determining if one of the first and second light intensities does not fall within a linear region of a characteristic curve of a light sensor; and determining a media type of the media based on a signal ratio of at least the first and second light intensities if it is determined that at least both of the first and second light intensities falls within the linear region of the characteristic curve of a light sensor, otherwise determining a media type of the media by extrapolating one of the first or second light intensities, which does not within the linear region of the characteristic curve of a light sensor, by projecting the one of the first or second light intensities onto a linear curve and then determining the media type based on a signal ratio of the one of the first or second light intensities that was not projected and the projected one of the first or second light intensities.

23. The media detection method of claim 22, wherein the projection of the one of the first or second light intensities includes increasing a duty cycle of a PWM signal controlling an intensity of a light source from D0 to an amount D1 where a detected increased light intensity corresponding to the one of the first or second light intensities falls within the linear region of the characteristic curve, and multiplying the increased one of the first or second light intensities by a ratio of D0 and D1.

24. The media detection method of claim 22, wherein the projection of the one of the first or second light intensities includes increasing an intensity of a light source from DO to an amount D1 where the increased one of the first or second light intensities falls within the linear region of the characteristic curve of a light sensor, and multiplying the increased one of the first or second light intensities by a ratio of DO and D1.

25. The media detection method of claim 22, wherein the measuring of the at least first and second light intensities radiating off of a media is performed prior to a picking of the media by a media manipulation device.

* * * * *